United States Patent [19]

Lee et al.

[11] Patent Number: 5,196,616
[45] Date of Patent: Mar. 23, 1993

[54] PROCESS FOR SEPARATING AND RECOVERING FLUOROCARBONS AND HYDROGEN FLUORIDE FROM MIXTURES THEREOF

[75] Inventors: Kung H. Lee, Chadds Ford, Pa.; Domenic J. Barsotti, Vineland, N.J.; Edward K. Sakata, Newark, Del.

[73] Assignee: E. I. Du Pont de Nemours and Company, Wilmington, Del.

[21] Appl. No.: 779,534

[22] Filed: Oct. 18, 1991

[51] Int. Cl.$^5$ .................. C07C 17/38; B01D 59/10
[52] U.S. Cl. .................................. 570/178; 55/16; 55/158; 203/39; 203/67; 423/483; 423/488
[58] Field of Search .............. 570/178; 423/483, 488; 203/39, 67; 55/16, 158

[56] References Cited

U.S. PATENT DOCUMENTS

| 3,947,558 | 3/1976 | van Eijl | 423/483 X |
| 4,424,067 | 1/1984 | Tarasenko et al. | 55/16 |
| 4,661,296 | 4/1987 | Grote et al. | 562/400 X |

FOREIGN PATENT DOCUMENTS 0884806  1/1988  Japan.

*Primary Examiner*—Marianne M. Cintins
*Assistant Examiner*—Michael B. Hydorn
*Attorney, Agent, or Firm*—James E. Shipley

[57] ABSTRACT

A process for separating and recovering an organic phase (e.g., fluorocarbons such as chlorofluorocarbons, hydrochlorofluorocarbons, hydrofluorocarbons and perfluorocarbons) from a feed stream of a mixture of fluorocarbons and hydrogen fluoride, wherein the mixture is characterized as forming at least one azeotrope or azeotrope-like composition involving at least one fluorocarbon and hydrogen fluoride, by passing the fluorocarbon/HF mixture feed stream through the feed side of a semipermeable membrane unit and then further separating a fluorocarbon-depleted hydrogen fluoride permeate stream and a fluorocarbon enriched residual stream exiting the membrane unit by conventional distillation. An essentially pure fluorocarbon phase and hydrogen fluoride phase are recovered from the distillation with the azeotrope or azeotrope-like distillate being recycled to the inlet of the semipermeable membrane unit.

14 Claims, 1 Drawing Sheet

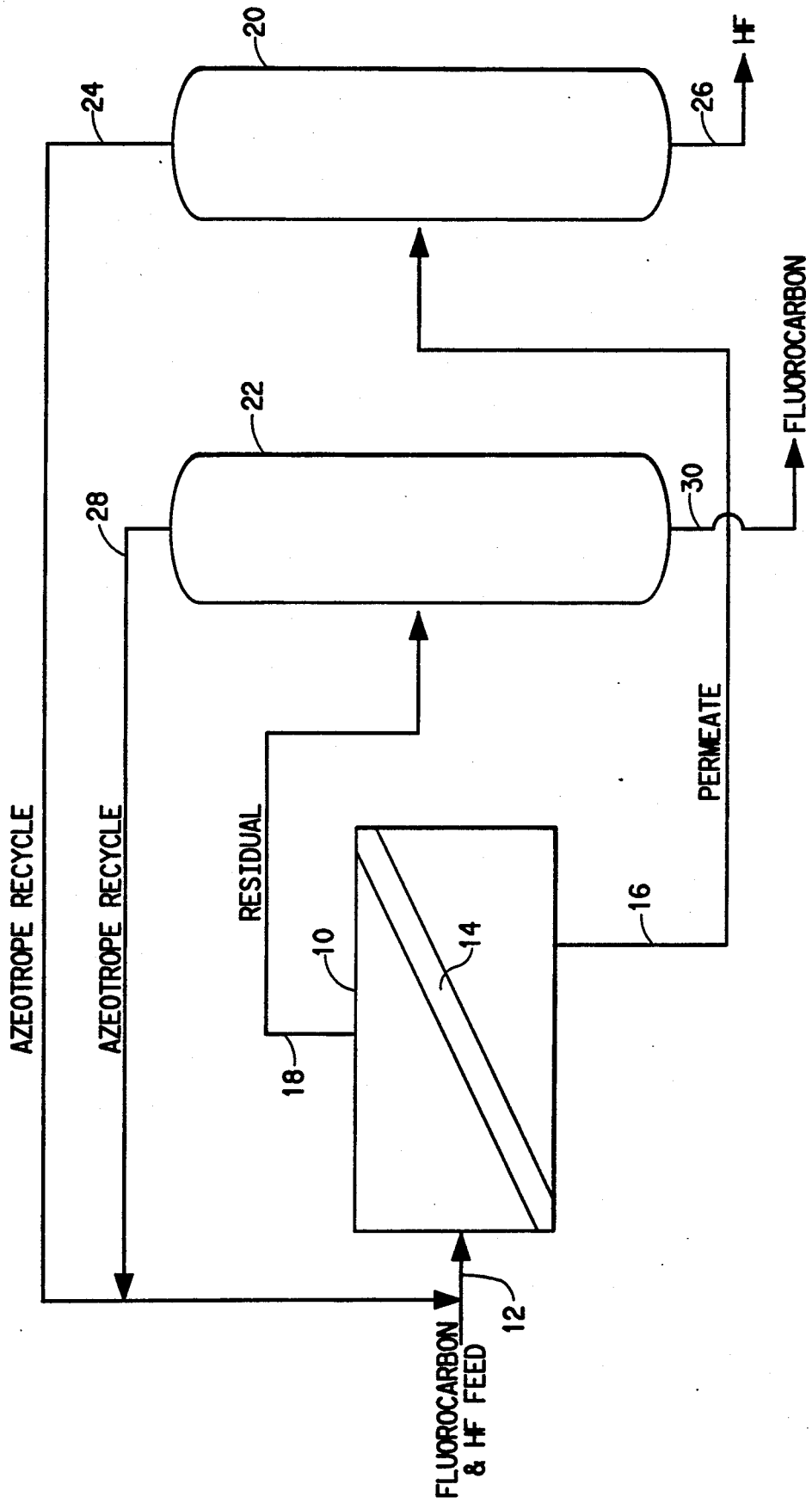

PROCESS FOR SEPARATING AND RECOVERING FLUOROCARBONS AND HYDROGEN FLUORIDE FROM MIXTURES THEREOF

BACKGROUND OF THE INVENTION

1. Field of the Invention

The present invention relates to an improved process for separating and recovering an organic phase (e.g., fluorocarbons) and hydrogen fluoride (HF) from a fluorocarbon/HF mixture, wherein because of the presence or potential formation of an azeotrope or azeotrope-like composition, it is impractical to separate the mixture by conventional distillation. More specifically, the present invention relates to separating a fluorocarbon/HF mixture, by use of a semipermeable membrane unit, into a HF depleted stream and a HF enriched stream that are then further processed individually by distillation.

2. Description of Related Art

It is well known that fluorochemicals of commercial interest including chlorofluorocarbons (CFC), hydrogen-containing chlorofluorocarbons (HCFC), hydrogen-containing fluorocarbons (HFC) and perfluorocarbons (FC) are typically manufactured by processes involving halogen exchange reactions. Generally the appropriate chlorocarbon is reacted with a fluorine-containing compound which serves as a fluorine donor. Most generally, the fluorine-donating source is hydrogen fluoride used in the presence of various catalytic compound. Such a process may be illustrated by the preparation of monochlorodifluoromethane (HCFC-22) wherein chloroform is the chlorocarbon employed and hydrogen fluoride is the fluorine source according to the following reaction:

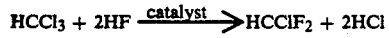

$$HCCl_3 + 2HF \xrightarrow{\text{catalyst}} HCClF_2 + 2HCl$$

The catalysts useful in this reaction include various metal oxides and halides and the reaction can be carried out in either vapor or liquid phase. The amount of hydrogen fluoride used in the above process is almost always in excess of the stoichiometric amount required and may be as much as a ten-fold excess. Excess hydrogen fluoride is used to increase yields and conversions and to reduce the reaction time. In the process illustrated by the above equation the crude reaction stream may contain some unreacted $HCCl_3$, underfluorinated $HCCl_2F$, the desired $HCClF_2$, the by-product HCl and the unreacted HF. By a combination of known processes such as distillation, phase separation and the like, hydrogen chloride can be recovered as useful anhydrous and/or aqueous hydrogen chloride, $HCCl_3$ and $HCCl_2F$ can be recovered for recycling as well as most of the hydrogen fluoride can be recovered by distillation processes. However, the desired product, $HCClF_2$ (HCFC-22), cannot be recovered free of hydrogen fluoride by ordinary distillation since HCFC-22 and HF form an azeotrope-like mixture (b.p. 50° C. at 292.5 psia and essentially constant composition of 97 wt. % HCFC-22 and 3 wt. % HF).

Various procedures have been proposed to recover HCFC-22 from its azeotropic mixture with HF, but these procedures introduce many undesirable problems. For example, an azeotropic mixture of HCFC-22 and HF can be washed with an aqueous alkali solution to convert HF into fluoride salt and thereby separate it from HCFC-22. HCFC-22 then requires dehydration and subsequent purification by distillation. The hydrogen fluoride neutralized by the alkali solution must be disposed of, creating disposal problems as well as representing loss of possibly recyclable reactant, thus having adverse economic effects.

Another possible procedure for recovering HCFC-22 from its azeotropic mixture with hydrogen fluoride is to contact the mixture with a concentrated sulfuric acid (as disclosed in U.S. Pat. No. 3,873,629) thereby to dissolve the hydrogen fluoride selectively in the sulfuric acid solution. Such a procedure also requires the additional steps of washing the thus separated HCFC-22 for the removal of the sulfuric acid, dehydration and then distillation. While the hydrogen fluoride dissolved in the concentrated sulfuric acid can be recovered for recycling by heating the sulfuric acid solution, such a recovery step requires specialized equipment and conditions such as are used in the hydrogen fluoride manufacturing process.

Van Eijl in U.S. Pat. No. 3,947,558 has suggested that hydrogen fluoride can be separated from an organic mixture of fluorinated $C_1$–$C_3$ compounds and recovered by selectively absorbing the HF in a glycol in which the HF is soluble, but the fluorinated organic compound is substantially insoluble. This process, as suggested by Van Eijl, depends upon very selective solubility differences between the fluorinated compounds and hydrogen fluoride. As exemplified by Van Eijl, even when the fluorinated compound is a perhalo compound, there is a fair degree of solubility of the perhalo compound in the glycol and a fair degree of solubility of the glycol in the perhalo compound. When the fluorinated compound is a hydrogen-containing chlorofluoro compound, such as HCFC-22, the solubility of HCFC-22 in the glycol is enhanced as well as the solubility of HF in the glycol-containing HCFC-22 layer and thus the separation process is adversely affected.

It has also been previously recognized that HF can be separated from certain non-azeotrope systems by selective permeation through a membrane. For example, Grote in U.S. Pat. No. 4,661,296 discloses separation of HF from a carbonylation process mixture (e.g., isobutyric acid, water and HF) using a "NAFION" membrane. The disclosed process is an alternative to separation by distillation. Also, Tarasenko in U.S. Pat. No. 4,424,067 discloses purification of anhydrous HF by removal of $AsF_3$ contaminant by permeation of the HF through non-porous fluoropolymer film. Again no separation of an azeotrope is suggested.

SUMMARY OF THE INVENTION

The present invention provides an improved process for separating and recovering an organic phase containing fluorocarbons (e.g., chlorofluorocarbons, hydrochlorofluorocarbons, hydrofluorocarbons and perfluorocarbons) and hydrogen fluoride phase from fluorocarbon/hydrogen fluoride mixtures, particularly mixtures wherein because of the presence or potential formation of an azeotrope or azeotrope-like composition, it is impractical to separate the mixture by conventional distillation. The improved method according to the present invention involves the simultaneous use of a membrane separation system in combination with conventional distillation systems, thus producing a hybrid recovery unit. In particular but not by way of limitation, this invention provides a process for the separation of a difficult-to-separate azeotrope or azeotrope-like composition consisting essentially of hydrogen fluoride and a $C_1$-$C_3$ fluorocarbon composition.

Thus the present invention provides a process for separating and recovering an organic phase and an hydrogen fluoride phase from a feed stream of a mixture of fluorocarbons and hydrogen fluoride wherein the mixture is characterized as forming at least one azeotrope or azeotrope-like composition involving at least one fluorocarbon and hydrogen fluoride, comprising the steps of:

(a) providing a semipermeable membrane means for separating fluorocarbons from hydrogen fluoride having a feed side and a permeate side wherein the semipermeable membrane means is characterized as having a fluorocarbon selectivity for allowing the passage of hydrogen fluoride relative to fluorocarbon organic phase of at least 3;

(b) passing a feed stream of fluorocarbons and hydrogen fluoride across the feed side of the semipermeable membrane such that hydrogen fluoride passes preferentially through the membrane to form a fluorocarbon-depleted hydrogen fluoride permeate stream and a fluorocarbon enriched residual stream;

(c) subjecting the fluorocarbon-depleted hydrogen fluoride permeate stream produced in step (b) to distillation, thus separating and recovering hydrogen fluoride; and (d) subjecting the fluorocarbon enriched residual stream produced in step (b) to distillation, thus separating and recovering a fluorocarbon organic phase.

According to one embodiment of the present invention, if either the permeate or the residual stream exiting the semipermeable membrane means is sufficiently pure that subsequent distillation is not necessary, only the other stream need be subjected to distillation. In one preferred embodiment according to the present invention, the fluorocarbon-depleted hydrogen fluoride permeate stream is further characterized as having a hydrogen fluoride concentration above that characteristic of the azeotrope or azeotrope-like composition involving hydrogen fluoride and the fluorocarbon such that the azeotrope or azeotrope-like composition is also separated and recovered in step (c) and wherein the fluorocarbon-enriched residual stream is further characterized as having a hydrogen fluoride concentration below that characteristic of the azeotrope or azeotrope-like composition involving hydrogen fluoride and the fluorocarbon such that the azeotrope or azeotrope-like composition is also separated and recovered in step (d) and wherein the azeotrope or azeotrope-like composition separated and recovered in steps (c) and (d) are recycled to the inlet side of the semipermeable membrane unit.

It is an object of the present invention to provide an effective and economical process for separating an azeotrope or an azeotrope-like mixture of hydrogen fluoride and a fluorocarbon composition. It is a further object of the present invention to provide a process for separating and recovering the components of an azeotrope or azeotrope-like mixture of hydrogen fluoride and a fluorocarbon composition which does not create any additional waste product disposal problems. It is a still further object to provide a separation process for an azeotrope or azeotrope-like mixture of hydrogen fluoride and a fluorocarbon composition which provides components in said azeotrope or azeotrope-like mixture in essentially pure forms. Fulfillment of these objects and the presence and fulfillment of other objects will be apparent upon complete reading of the specification and claims taken in conjunction with the attached drawing.

BRIEF DESCRIPTION OF THE DRAWING

The FIGURE represents a schematic illustration of a typical improved process for recovery of organic vapors according to one embodiment of the present invention.

DESCRIPTION OF THE PREFERRED EMBODIMENTS

The feed stream to be separated according to the improved process of the present invention can, in the broadest sense, be any mixture of at least one fluorocarbon and hydrogen fluoride that results in a fluorocarbon/HF admixture that is difficult to separate by conventional distillation. Hence, for purposes of the present invention, fluorocarbon refers broadly to any chlorofluorocarbon, hydrochlorofluorocarbon, hydrofluorocarbon, perfluorocarbon (i.e., CFC, HCFC, HFC, and FC, respectively) or mixtures thereof that form or tend to form a mixture with HF that is difficult to separate by conventional distillation. As such, the term fluorocarbon is intended to include halocarbons that form or tend to form true azeotropes with HF as well as halocarbons that form or tend to form azeotrope-like compositions with HF. In other words, the feed stream according to the present invention does not have to be at the azeotrope or azeotrope-like concentration range, per se, but merely capable of forming the difficult-to-separate composition during distillation (all as explained more fully later).

For purposes of the present invention the term azeotrope refers to a constant boiling admixture of one or more fluorocarbons with HF, whose admixture behaves as a single substance, in that the vapor, produced by partial evaporation or distillation of the liquid has the same composition as the liquid, i.e., the admixture distills without compositional change. Analogously, the term azeotrope-like, for purposes of this invention, refers generally to any such mixture of one or more fluorocarbons and HF that exhibits essentially a constant composition on boiling (i.e., distills with little or no change in the composition due to closeness of the boiling points of the components in the mixture or due to some other reasons).

The fluorocarbons of particular use in the present invention include, by way of example but not limited thereto, the aliphatic halocarbon of 1 to 3 carbon atoms containing at least one fluorine atom substituent. Thus, the term fluorocarbon will include chlorofluorocarbon, hydrogen-containing chlorofluorocarbon, perfluorocarbon and hydrogen-containing fluorinated hydrocarbon of from 1 to 3 carbon atoms and mixtures thereof. More specifically, fluorocarbons of particular interest include:

chlorodifluoromethane ($CHClF_2$, HCFC-22)
difluoromethane ($CH_2F_2$, HFC-32)
1,2-dichloro-1,1,2,2-tetrafluoroethane ($CClF_2CClF_2$, CFC-114)
1,1-dichloro-1,2,2,2-tetrafluoroethane ($CF_3CCl_2F$, CFC-114a)
2,2-dichloro-1,1,1-trifluoroethane ($CF_3CHCl_2$, HCFC-123)
2-chloro-1,1,1,2-tetrafluoroethane ($CF_3CHClF$, HCFC-124)
pentafluoroethane, ($CF_3CHF_2$, HFC-125)
1,1,2,2-tetrafluoroethane ($CHF_2CHF_2$, HFC-134)

1,1,1,2-tetrafluoroethane ($CF_3CH_2F$, HFC-134a)
1,1-dichloro-1-fluoroethane ($CCl_2FCH_3$, HCFC-141b)
1-chloro-1,1-difluoroethane ($CClF_2CH_3$, HCFC-142b)
2-chloro-1,1,1-trifluoroethane ($CF_3CH_2Cl$, HCFC-133a)

In addition to the separation of individual fluorocarbon/HF mixtures, the improved process of the present invention is particularly useful in separating and recovering mixtures of fluorocarbons in the presence of HF. Frequently commercial production of a fluorocarbon involves a sequential fluorination of a starting chlorocarbon resulting in a distribution of reaction products and intermediates, all of which tend to make the mixture even more complex and difficult to isolate and recover by conventional separation techniques. Thus various mixtures of the 120 hydrofluoroethane series are frequently found together such as a mixture of HCFC-123, HCFC-124 and HFC-125 or a mixture of HCFC-124 and HFC-125. Since virtually all fluorocarbons of the 120 series form azeotropes with HF (i.e., 10 HF mole % with 125, 6.5 HF mole % with 124, and 60 HF mole % with 123) the distillation of such a mixture is not an acceptable method of separation. Similarly, a mixture of CFC-114a, HCFC-124 and HFC-134a or a mixture of HCFC-124 and HFC-134a are commercially found together (wherein HFC-134a forms an azeotrope in the 4 to 7 HF mole % range). These mixtures are particularly amenable to the benefits of the present invention in that separation and recovery by distillation is virtually impossible as is the alternative of liquid/liquid low temperature phase separation.

In contrast to the above distillation or liquid/liquid phase separation methods, the present invention provides a separation process for difficult-to-separate fluorocarbon compositions containing hydrogen fluoride which process does not require addition of any extraneous components, does not alter any of the components of the fluorocarbon composition and which does not create any additional waste disposal problems. In essence, in the present invention the difficult-to-separate fluorocarbon composition is initially treated with a selected non-porous, semi-permeable polymer membrane which provides two components, each of which is enriched in one or the other of the components in the original composition (i.e., either the organic phase or hydrogen fluoride phase). Subsequent treatment, such as distillation of the two compositions, can then provide the components of the original composition in essentially purified forms.

The present invention may perhaps be best explained and understood by reference to the drawing and by illustrating the separation of an azeotropic mixture of hydrogen fluoride (HF) and chlorodifluoromethane (HCFC-22) relative to the FIGURE. As previously mentioned, HCFC-22 is usually manufactured by the process of fluorinating chloroform with excess HF in the presence of certain metallic compounds as catalysts, e.g., antimony halide. In other preliminary purification processes involving mostly distillation, a mixture of HCFC-22 and HF is obtained which cannot be separated readily by distillation into pure components since HCFC-22 and HF form an azeotropic mixture containing about 97 wt. % HCFC-22 and 3 wt. % HF. As also mentioned, under present practices, such an azeotrope mixture is usually treated with an aqueous alkali solution to remove HF from the mixture; the HCFC-22 layer is then washed, dried and distilled to provide purified HCFC-22. Such a process results in the loss of HF for recycling back to the manufacturing process and additionally creates a problem of fluoride disposal.

In contrast and as conceptually illustrated in the FIGURE, in the present invention the above azeotropic mixture of HCFC-22 and HF is typically continuously introduced into a membrane separation unit 10 via inlet 12 as the fluorocarbon/HF feed stream. Within the separation unit 10, the feed stream makes contact with selected non-porous, semi-permeable polymer membrane 14. Because of the preferential permeability of HF across the membrane 14, the separation unit 10 produces a permeate stream exiting via line 16 wherein the concentration of HF is enriched typically about ten-fold or more relative to its composition in the azeotrope feed concentration. Simultaneously a non-permeate residual stream is continuously withdrawn via line 18 wherein the HF concentration is proportionally depleted relative to the original feed composition. Thus in the HCFC-22/HF azeotrope illustration a typical feed stream to the membrane unit 10 would be at approximately 25° C. and about 200 psig and would contain about 3 wt. % HF. The residual stream exiting outlet 18 would have a HF concentration reduced to around 0.3 wt. % representing substantial one-pass recovery.

By taking advantage of the fact that the fluorocarbon (HCFC-22 the illustrated embodiment) and HF form an azeotrope, purified fluorocarbon and purified HF can be recovered by subsequent distillation steps. Thus, the permeate composition exiting the membrane unit 10 via line 16 can be distilled in column 20. The small amount of fluorocarbon/HF azeotrope being distilled overhead is then recycled via line 24 to the feed side of the permeation unit 10 and essentially purified HF can be recovered as distillation bottom via line 26. In the illustrated processing of an azeotrope stream associated with the manufacture of HCFC-22 the HF from the distillation column 20 can be recycled to the HCFC-22 manufacturing process. Similarly, the non-permeate residual composition exiting the membrane unit 10 via line 18 is distilled in column 22. The small amount of fluorocarbon/HF azeotrope being distilled over head is recycled via line 28 to the feed side of the permeation unit 10 and purified fluorocarbon (HCFC-22)is recovered via line 30 from the distillation bottom. Of course, both HF and HCFC-22 can be subjected to further purification if desirable. Also, if either of the residual or permeate streams can be utilized without subsequent distillation, then one of the columns can be eliminated and a single column in combination with the membrane unit can be employed and should be considered an equivalent process for purposes of this invention.

The non-porous, semi-permeable polymer film useful in the present invention for the permeation step of the process may be any hydrogen fluoride-resistant polymeric material which can be formed into a thin non-porous film and exhibits the desired selective permeability as defined latter. For a polymer to be resistant to degradation upon prolonged contact with HF, it is preferred that the polymers are fluorinated polymers and include, among others, fluorinated ethylene-propylene copolymers, poly(ethylene-chlorotrifluoroethylene), poly(chlorotrifluoroethylene), poly(tetrafluoroethylene), copolymers of ethylene and tetrafluoroethylene, poly(vinylidene fluoride), poly(perfluorovinyl ethers) and the like. Preferred are the fluorinated polymers containing groups such as carboxyl or sulfonyl such as described in U.S. Pat. Nos. 3,282,875; 3,718,627; and 4,329,435. Particularly preferred perfluorinated membranes useful in the present invention are the fluorinated polymers containing sulfonic acid groups sold under the name "NAFION" by Du Pont and derived from copolymerizing tetrafluorethylene and a perfluorovinylether which contains a sulfonic acid group or derivative thereof. Thus, the preferred membranes are characterized structurally as copolymers containing the following recurring units:

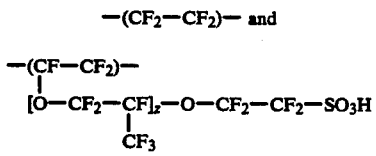

where z is an integer of 1 or greater. These "NAFION" membranes have a high permeation rate for HF and at the same time are highly resistant to degradation by HF.

The salt or partial salt forms (e.g., —SO$_3$Na and —SO$_3$K) of the above polymer are found to be equally effective in achieving the desired selective permeability.

The semipermeable membrane unit (the permeator) useful in the present invention can be generally any such device as well known in the art, including by way of example, but not limited thereto, semipermeable membrane thin layer of film (i.e., the so-called plate and frame unit), spiral wound membrane, hollow fiber semipermeable membrane or the like (including combinations of such devices). For the semipermeable membrane to separate the fluorocarbon/HF mixture into a HF enriched permeate stream and a HF deplete residual stream, there must be a difference or selectivity in the permeation rates for the hydrogen fluoride and organic fluorocarbon phases. For purposes of this invention the necessary preferential permeation rate for the hydrogen fluoride through the barrier membrane relative to the permeation rate for fluorocarbon phase can be satisfied and/or confirmed by considering the increase in HF concentration in the permeate relative to the concentration of HF in the feed stream. This parameter, for purposes of this invention hereinafter referred to as selectivity, can vary from as little as 3 but is more typically 10 or greater and is frequently higher than 20. Preferably this selectivity should be 10 or greater.

In the permeation separation process, two parameters are usually considered as variables to enhance the separation process; i.e., the temperature and the pressure differential between the feed side of the permeation membrane and the permeate side of the membrane. While increasing the pressure differential appears to have some effect upon the separation of HF and fluorocarbon, the enhancement in the separation is not very great. Thus again by way of example but not limited thereto, in a composition of 3 wt. % HF and 97 wt. % HCFC-22, increasing the pressure differential from atmospheric to 150 psig resulted in less than a four-fold increase in the HF content in the permeate. A four-fold concentration increase of HF across the membrane is considered just marginal to efficient separation. However it has now been found that with turbulent flow of a HF/HCFC-22 mixture in a thin layer across the permeation membrane a separation is achieved which gave as much as a twenty-fold increase in the HF concentration in the permeate. The turbulent flow for purposes of this invention is characterized by a Reynolds Number of at least 2,000. Such a concentration increase by permeation provides a good potential for the separation of HF from HCFC-22.

The following examples are presented to further illustrate specific embodiments of the invention. In presenting these examples all references to percentages of components are by weight percent unless otherwise indicated.

EXAMPLE 1

Separation of HF and HCFC-22 was carried out using "NAFION" perfluorinated membrane (Du Pont) of 1 mil thickness. The membrane on a support was placed in a circular device which could be clamped airtight. The clearance above the surface of the membrane was approximately 0.7 cm (0.276 inches). The total surface of the membrane exposed to the feed of HCFC-22/HF mixture was 0.104 sq. ft.

A mixture of HF and HCFC-22 was prepared in a cylinder and appropriate valves were installed to monitor the flow of HCFC-22/HF out of the cylinder. The feed from the cylinder entered the permeation device through a 1/16" stainless steel tubing located directly opposite the feed outlet so that the HCFC-22/HF mixture from the feed tube would move across the membrane surface and then exit the device via the second stainless steel tubing.

The gas exiting the permeation device was contacted with a column containing ultra-pure potassium carbonate to trap HF and HCFC-22 was collected in a polyethylene or a stainless steel cylinder. After the separation run was finished, the column containing potassium carbonate was disconnected, and the potassium carbonate was dissolved in a known volume of deionized water.

Using a fluoride ion specific electrode, the fluoride ion content was determined and expressed as HF. HCFC-22 was determined by gas chromatography. Suitable valves were provided in the exit stream to control pressure, feed flow, etc.

Similarly, the permeate stream coming through the membrane was passed into a column containing ultra-pure potassium carbonate to trap HF and then HCFC-22 was collected in an evacuated stainless steel cylinder. The analysis of the potassium carbonate for fluoride and of HCFC-22 in the collection cylinder provided a composition of the permeate.

Material balance was made by comparing the total weight of the HF in the permeate and the non-permeate and the total weight of HCFC-22 in the permeate and the non-permeate with the total amount of HF and HCFC-22 taken from the original feed cylinder.

The results are given in Table 1.

TABLE 1

| Feed Composition: | 3 wt. % HF and 97 wt. % HCFC-22 |  |
|---|---|---|
|  | Pressure |  |
|  | Feed Side: 130–140 psig |  |
| Temp = Ambient | Permeate Side: About 22" |  |
| (about 20° C.) | Hg Vac |  |
| Feed Rate | HF Content (wt. %) in | |
| g/sq.ft./hr | non-permeate | permeate |
| 500 | 0.4 | 16 |
| 2000 | 1.1 | 32 |
| 8000 | 1.7 | 63 |
| 10100 | 1.8 | 70 |

The above results clearly show that HF and HCFC-22 can be separated from their azeotropic mixture. Thus, after the preliminary separation using the "NA- FION" perfluorinated membrane separation, the permeate can be distilled to remove HCFC-22 as HCFC-22/HF azeotrope, leaving behind essentially pure HF, and similarly the non-permeate fraction can also be distilled to remove the HF as HCFC-22/HF azeotrope, leaving behind the essentially pure HCFC-22.

EXAMPLE 2

Separation of an azeotropic mixture of HF and HCFC-22 which contains 2.8 wt. % HF and 97.2 wt. % HCFC-22 may be illustrated by this Example. Using a permeation membrane of "NAFION" perfluorinated membrane having a surface area of approximately 2.64 sq. ft., the above composition of HCFC-22/HF mixture will be passed over the permeation membrane at a rate of 8000 g/(sq.ft.×hr.) or a total of 21,114 g/hr. at approximately 20° C. and 130–140 psig feed pressure and a permeate side pressure of approximately 20" Hg vac. At this feed rate, 591 g of HF and 20,523 g of HCFC-22 will be introduced into the permeator (i.e., membrane unit) per hour.

The permeate will be 378 g/hr. of which 228 g (60.3 wt. %) was HF. This permeate stream will then be distilled to provide 154 g/hr. of distillate of the azeotropic composition (2.8 wt. % HF and 97.2 wt. % HCFC-22)and a distillation residue of substantially pure HF at a rate of 224 g/hr.

The non-permeate from the permeation separation will be 20,736 g/hr. of which 363 g (1.75 wt. %) will be HF and 20,373 g (98.25 wt. %) will be HCFC-22. Distillation of this non-permeate stream provides 12,960 g/hr. of an azeotropic mixture of which 363 g is HF and 12,597 g is HCFC-22. The distillation residue is substantially pure HCFC-22 at a rate of 7776 g per hour.

The azeotropic distillates from both the distillation of the permeate and the non-permeate is to be recycled to the feed side of the permeation separator. As is clear from this Example, the present separation process is advantageously carried out as a continuous process and, as this Example illustrates, an azeotropic mixture of HF and HCFC-22 can be completely separated into its pure components with little or no contribution to fluoride waste disposal problems.

EXAMPLE 3

Separation of an azeotrope-like mixture of HF, pentafluoroethane (HFC-125) and monochlorotetrafluoroethane (HCFC-124) which contains 5 wt. % HF and 95 wt. % organic (i.e., HFC-125 and HCFC-124), may be illustrated by this Example using a permeation membrane of "NAFION" perfluorinated membrane having a surface area of approximately 2.27 sq. ft. The above compositions of (HCFC-125 & HCFC-124)/HF is passed over the permeation membrane at a total rate of 2,835 g/hr. at ambient temperature (about 20° C.), feed pressure 100 to 105 psig and permeate pressure of about 22" Hg vac. At this feed rate, 141.7 g HF and 2,693.3 g of organics is introduced into the permeator per hour.

The permeate was 121 g/hr. of which 101 g (83 wt. %) will be HF and 20 g (17 wt. %) will be organics. This permeate stream will then be distilled to provide 21 g/hr. of distillate of the azeotrope-like compositions (5 wt. % HF and 95 wt. % organics) and a distillation residue of substantially pure HF at a rate of 100 g/hr.

The non-permeate from the permeation separator will be 2,714.3 g/hr. of which 40.7 g (1.5 wt. %) will be HF and 2,673.6 g (98.5 wt. %) will be organics. Distillation of this non-permeate stream will provide 814 g/hr. of an azeotrope-like mixture of which 40.7 g will be HF and 773.3 g will be organics. The distillation residue will be substantially pure organics at a rate of 1,900 g/hr. which can be further separated into individual organic components by simple conventional distillation.

The azeotropic distillates from both the distillation of the permeate and the non-permeate are recycled to the feed side of the permeation separator. As is clear from this Example, the present separation process is advantageously carried out as a continuous process and, as this Example illustrates, an azeotrope-like mixture of (HFC-125 & HCFC-124)/HF can be separated into pure components with little or no contribution to the fluoride waste disposal problem.

EXAMPLE 4

Separation of an azeotrope-like mixture of HF, tetrafluoroethane (HFC-134a) and monochlorotetrafluoroethane (HCFC-124), which contains 0.7 wt. % HF and 99.3 wt. % organics (i.e., HFC-134a and HCFC-124), may be illustrated by this Example. Using a permeation membrane of "NAFION" perfluorinated membrane having a surface area of approximately 8.7 sq. ft., the above compositions of (HFC-134a & HCFC-124)/HF will be passed over the permeation membrane at a rate of 2,000 g/sq.ft./hr. or a total rate of 17,377 g/hr. at ambient temperature (about 20° C.), feed pressure about 65 psig and permeate pressure of about 22" Hg vac. At this feed rate, 122 g HF and 17,257 g of organics will be introduced into the permeator per hour.

The permeate will be 17.6 g/hr. of which 14 g (80 wt. %) will be HF and 3.6 g (20 wt. %) will be organics. The permeate stream will then be distilled to provide 3.6 g/hr. of distillate of the azeotrope-like compositions (0.7 wt. % HF and 99.3 wt. %) organics) and a distillation residue of substantially pure HF at a rate of 14 g/hr.

The non-permeate from the permeation separator will be 17,359 g/hr. of which 108 g (0.62 wt. %) will be HF and 17,251 g (99.38 wt. %) will be organics. Distillation of this non-permeate stream will provide 15,375 g/hr. of an azeotrope-like mixture of which 108 g will be HF and 15,267 g will be organics. The distillation residue will be substantially pure organics at a rate of 1,984 g/hr., which can be further separated into individual organic components by simple conventional distillation.

The azeotropic distillates from which both the distillation of the permeate and non-permeate are recycled to the feed side of the permeation separator. As is clear from this Example, the present separation process is advantageously carried out as a continuous process and, as this Example illustrates, an azeotrope-like mixture of (HFC-134a & HCFC-124)/HF can be separated into pure components with little or no contribution to the fluoride waste disposal problem.

Having thus described and exemplified the invention with a certain degree of particularity, it should be appreciated that the following claims are not to be so limited but are to be afforded a scope commensurate with the wording of each element of the claim and equivalents thereof.

We claim:

1. A process for separating and recovering a fluorocarbon phase and a hydrogen fluoride phase from a feed stream of a mixture of fluorocarbon and hydrogen fluoride wherein said mixture is characterized as forming at least one azeotrope or azeotrope-like composition involving at least one fluorocarbon and hydrogen fluoride, comprising the steps of:

(a) providing a semipermeable membrane means for separating fluorocarbon from hydrogen fluoride having a feed side and a permeate side wherein said semipermeable membrane means is characterized as having a selectivity for allowing the passage of hydrogen fluoride relative to the fluorocarbon phase of at least 3;

(b) passing a feed stream of fluorocarbon and hydrogen fluoride across the feed side of the semipermeable membrane such that hydrogen fluoride passes preferentially through the membrane thus forming a fluorocarbon-depleted hydrogen fluoride permeate stream and a fluorocarbon enriched residual stream;

(c) subjecting said fluorocarbon-depleted hydrogen fluoride permeate stream produced in step (b) to distillation, thus separating and recovering hydrogen fluoride; and (d) subjecting said fluorocarbon enriched residual stream produced in step (b) to distillation, thus separating and recovering a fluorocarbon phase.

2. A process of claim 1 wherein said fluorocarbon-depleted hydrogen fluoride permeate stream is further characterized as having a hydrogen fluoride concentration above that characteristic of the azeotrope or azeotrope-like composition involving at least one fluorocarbon and hydrogen fluoride such that at least a portion of any remaining azeotrope or azeotrope-like composition involving at least one fluorocarbon and hydrogen fluoride is also separated and recovered in step (c) and wherein said fluorocarbon-enriched residual streams is further characterized as having a hydrogen fluoride concentration below that characteristic of the azeotrope or azeotrope-like composition involving at least one fluorocarbon and hydrogen fluoride such that at least a portion of any remaining azeotrope or azeotrope-like composition involving at least one fluorocarbon and hydrogen fluoride is also separated and recovered in step (d) and wherein at least a portion of any of said remaining azeotrope or azeotrope-like composition involving at least one fluorocarbon and hydrogen fluoride separated and recovered in steps (c) and (d) is recycled to the inlet side of said semipermeable membrane unit.

3. A process of claim 1 wherein the fluorocarbon is selected from the group consisting of $C_1$ to $C_3$ chlorofluorocarbons, hydrochlorofluorocarbons, hydrofluorocarbons and perfluorocarbons.

4. A process of claim 2 wherein the fluorocarbon is selected from the group consisting of $C_1$ to $C_3$ chlorofluorocarbons, hydrochlorofluorocarbons, hydrofluorocarbons and perfluorocarbons.

5. A process of claim 1 wherein the fluorocarbon is difluoromethane.

6. A process of claim 2 wherein the fluorocarbon is difluoromethane.

7. A process of claim 1 wherein the fluorocarbon is chlorodifluoromethane.

8. A process of claim 2 wherein the fluorocarbon is chlorodifluoromethane.

9. A process of claim 1 wherein the fluorocarbon is a mixture of 2-chloro-1,1,1,2-tetrafluoroethane and 1,1,1,2-tetrafluoroethane.

10. A process of claim 2 wherein the fluorocarbon is a mixture of 2-chloro-1,1,1,2-tetrafluoroethane and 1,1,1,2-tetrafluoroethane.

11. A process of claim 1 wherein the fluorocarbon is a mixture of 2-chloro-1,1,1,2-tetrafluoroethane and pentafluoroethane.

12. A process of claim 2 wherein the fluorocarbon is a mixture of 2-chloro-1,1,1,2-tetrafluoroethane and pentafluoroethane.

13. A process for separating and recovering a fluorocarbon phase and a hydrogen fluoride phase from a feed stream of a mixture of fluorocarbon and hydrogen fluoride wherein said mixture is characterized as forming at least one azeotrope or azeotrope-like composition involving at least one fluorocarbon and hydrogen fluoride, comprising the steps of:

(a) providing a semipermeable membrane means for separating fluorocarbon from hydrogen fluoride having a feed side and a permeate side wherein said semipermeable membrane means is characterized as having a selectivity for allowing the passage of hydrogen fluoride relative to the fluorocarbon organic phase of at least 3;

(b) passing a feed stream of fluorocarbon and hydrogen fluoride across the feed side of the semipermeable membrane such that hydrogen fluoride passes preferentially through the membrane thus forming a fluorocarbon-depleted hydrogen fluoride permeate stream and a fluorocarbon enriched residual stream; and (c) subjecting said fluorocarbon-depleted hydrogen fluoride permeate stream produced in step (b) to distillation, thus separating and recovering hydrogen fluoride.

14. A process for separating and recovering a fluorocarbon phase and a hydrogen fluoride phase from a feed stream of a mixture of fluorocarbon and hydrogen fluoride wherein said mixture is characterized as forming at least one azeotrope or azeotrope-like composition involving at least one fluorocarbon and hydrogen fluoride, comprising the steps of:

(a) providing a semipermeable membrane means for separating fluorocarbon from hydrogen fluoride having a feed side and a permeate side wherein said semipermeable membrane means is characterized as having a selectivity for allowing the passage of hydrogen fluoride relative to the fluorocarbon organic phase of at least 3;

(b) passing a feed stream of fluorocarbon and hydrogen fluoride across the feed side of the semipermeable membrane such that hydrogen fluoride passes preferentially through the membrane thus forming a fluorocarbon-depleted hydrogen fluoride permeate stream and a fluorocarbon enriched residual stream; and (c) subjecting said fluorocarbon enriched residual stream produced in step (b) to distillation, thus separating and recovering a fluorocarbon phase.

* * * * *